(12) United States Patent
Niedermeier

(10) Patent No.: US 7,667,846 B2
(45) Date of Patent: Feb. 23, 2010

(54) DEVICE AND PROCESS FOR INSPECTING THE BOTTOMS OF CONTAINERS

(75) Inventor: Anton Niedermeier, Offenstetten (DE)

(73) Assignee: Krones AG, Neutraubling (DE)

( * ) Notice: Subject to any disclaimer, the term of this patent is extended or adjusted under 35 U.S.C. 154(b) by 78 days.

(21) Appl. No.: 11/965,311

(22) Filed: Dec. 27, 2007

(65) Prior Publication Data

US 2008/0158554 A1 Jul. 3, 2008

(30) Foreign Application Priority Data

Dec. 29, 2006 (DE) ........................ 10 2006 062 575

(51) Int. Cl.
*G01N 21/00* (2006.01)
(52) U.S. Cl. ................. 356/428; 356/239.4; 356/239.7; 356/240.1
(58) Field of Classification Search ... 356/239.1–239.4, 356/426–428
See application file for complete search history.

(56) References Cited

U.S. PATENT DOCUMENTS

| 4,943,713 A | | 7/1990 | Yoshida et al. | |
| 4,959,537 A | | 9/1990 | Kimoto et al. | |
| 5,404,227 A | * | 4/1995 | Sumita et al. | ............... 356/428 |
| 7,057,718 B2 | | 6/2006 | Kwirandt et al. | |
| 2005/0248766 A1 | | 11/2005 | Niedermeier et al. | |

FOREIGN PATENT DOCUMENTS

| DE | 3839682 | 6/1989 |
| DE | 3919110 | 12/1989 |
| DE | 10133104 | 1/2003 |
| EP | 0585 821 A1 | 3/1994 |
| EP | 0 620 430 A1 | 10/1994 |
| EP | 0 701 117 A2 | 3/1996 |
| JP | 2003-322623 | 11/2003 |

OTHER PUBLICATIONS

European Search Report based on European Patent Application No. 07 021 762.5 ; Date of Mailing: Apr. 15, 2008.

* cited by examiner

*Primary Examiner*—Michael P Stafira
(74) *Attorney, Agent, or Firm*—Marshall, Gerstein & Borun LLP

(57) ABSTRACT

A system for inspecting container bottoms with an observation device, which observe the container bottoms, with a plurality of viewing windows, which are arranged underneath the container bottoms and which have viewing sections, through which the observation device observes the container bottoms, where the viewing windows are mounted in a carrier plate. Also, holding devices are provided, which transport the containers a certain distance above the carrier plate, and the viewing sections are at least partially offset from a projection of the containers in a direction perpendicular to the carrier plate.

11 Claims, 3 Drawing Sheets

DEVICE AND PROCESS FOR INSPECTING THE BOTTOMS OF CONTAINERS

CROSS-REFERENCE TO RELATED APPLICATION

The present application claims the benefit of priority of German Patent Application No. 10 2006 062 575.7 filed Dec. 29, 2006. The entire text of the priority application is incorporated herein by reference in its entirety.

FIELD OF THE DISCLOSURE

The present disclosure pertains to a system and to a process for inspecting the bottoms of containers, such as used in beverage bottling operations.

BACKGROUND

Systems of this type are known in the state of the art. There exists a basic need to check filled containers for contamination such as shards of glass or other insoluble forms of organic or inorganic dirt in the product. For this purpose, many different systems are known according to the state of the art. Most of the optical inspection systems are based on the idea of bringing the contamination, such as a glass shard, into several different positions and of comparing several pictures of the container with each other, as a result of which the presence of the glass shard can be detected. These types of systems are known by the collective term "full bottle inspection" (FBI).

To change the position of the foreign body, the containers are put in motion; in some cases they are swirled, and in others they are rotated around the longitudinal axis of the bottle. When such movements are conducted close in time to the detection process, however, it is possible for water, belt lubricant, and occasionally the product itself (in the case of containers which have broken or have leaks) to be sprayed onto the glass guard of the optical sensor, which is usually a camera. The glass guard therefore become dirty.

The constant contamination of the glass guard is a fundamental problem in the process of inspecting containers as described above. The view of the container degrades over the course of time, and the detection quality decreases correspondingly. It is therefore known in the state of the art that the glass guard can be cleaned regularly. When this cleaning is done manually, however, the down times are increased considerably, and the efficiency of the machine is decreased. In the case of automatic cleaning, the effect of the cleaning operation is often unsatisfactory. In certain machines, the optical monitoring system inspects the bottoms of the containers through the glass guard of the camera, which is brought directly underneath the container bottom. Any moisture which drops off the container thus falls directly onto the glass guard, as a result of which, over time, the view becomes impaired and an error can be detected when none actually exists. In practice, this means that at the glass guards must be cleaned at least once very 8 hours of operating time. When bottles break in the machine, the frequency of the cleanings must be increased.

It has also been found that, when, for example, a container bursts in the inspection carousel or near it, the nearby glass guards become dirty. Another contamination factor is derived from the fact that the inspection carousels known according to the state of the art pass below the acceleration carousels in the area where the containers are transferred. These acceleration carousels are used to accelerate the containers by means of rotational movement, for example. In this case, lubricant and dirt from the drive units can fall onto the glass guards. Because abrasion also occurs, dirt can arrive on the glass guard for this reason as well.

SUMMARY OF THE DISCLOSURE

The present disclosure is therefore based on the task of providing a system which reduces the effort required to clean the glass guards. In particular, a system is to be made available which makes use of certain design measures to reduce the degree to which the glass guards become contaminated over the course of time.

The disclosed system for inspecting the bottoms of containers has an observation device, which observes the bottoms of the containers. In addition, a plurality of viewing windows is provided, which are arranged underneath the container bottoms and which have viewing sections, through which the observation device observes the container bottoms. The viewing windows are mounted in a carrier plate.

According to the disclosure, holding devices are provided, which transport the containers a certain distance above the carrier plate, where the viewing windows are at least partially offset from a projection of the containers in a plane perpendicular to the carrier plate.

The projection of the containers results in a plane which is perpendicular to the carrier plate and exactly underneath the containers.

As a result of the offset arrangement of the viewing sections or preferably of the entire viewing windows, the dirt which falls from the containers essentially in the vertical direction will not land on the viewing sections.

Preferably the viewing sections or even more preferably the entire viewing windows are arranged completely outside the projection of the containers.

The holding devices preferably transport the containers along a predetermined path of any desired geometry, and the individual viewing sections will be offset from this path. Thus the containers could be transported along a straight line, for example, and the viewing windows would therefore be arranged parallel to this straight line along another straight line. The idea of an "offset arrangement" of the viewing sections with respect to the path of the containers should be understood to mean that preferably there is no section of the viewing window which is located directly underneath the path. In this embodiment, the center of each viewing window or the center of each viewing section is shifted away from the path along which the containers are transported.

It would also be possible, however, for the containers to be transported along a certain path and for the viewing windows to be arranged along this same path also, but again with an offset to the projections in question. In this case, a viewing section would preferably follow each projection of the containers, and the containers and the viewing sections would alternate with each other.

Holding devices are preferably provided which transport the containers at least over certain distances along a first circular path with a predetermined radius, where the viewing sections are arranged at an offset in the radial direction from this circular path, preferably on the radially inner side of the circular path.

In other words, the viewing window or the glass guard is removed from the area around the assigned container holder, i.e., the area most at risk of contamination, as a result of which the contaminating particles falling off the containers do not land on the viewing window but rather on areas of the carrier plate adjacent to the window. The effect which the dirt exerts on these adjacent areas and especially on the adjacent nontransparent areas of the carrier plate is not as detrimental as that which it would have on the viewing window, since there it would cause direct interference with the inspection of the containers. It is especially preferred that the inspection device, especially a camera, be located underneath the viewing windows.

In another preferred embodiment, the carrier plate has a circular cross section, and the viewing windows are arranged around a second circular path, where this second circular path has a radius different from the radius of the first circular path, preferably a radius smaller than that of the first path. In other words, the viewing windows are arranged at equal distances from the first circular path, and thus the offset is uniform.

It is especially preferred for the offset to be at least large enough to ensure that there is no longer any area of the viewing window which is underneath the containers during operation.

It is advantageous for the holding devices to be attached to the carrier plate in an essentially stationary manner. This means that the holding devices move at the same speed as the carrier plate and thus that the containers do not move relative to the observation devices.

It is especially preferred for precisely one observation device with precisely one viewing section to be assigned to at least one holding device. This means that the number of viewing windows and viewing sections is equal to the number of observation devices or cameras, and these cameras are stationary relative to the viewing windows. In this way, a camera can take several pictures of the same container at different times and in this way determine the presence of foreign bodies in the container.

At least one spray shield device, which at least partially and preferably completely encloses the viewing windows, is preferably provided above the carrier plate. This spray shield device, which is also called a spray water trap in the following, can be used to keep away contamination coming from various directions or from adjacent stations and to block spray water coming from the upstream acceleration carousel. It is especially preferred for the spray shield device to have at least one opening facing the container bottom. More precisely, the observation device observes the container bottom through this opening and through the viewing window; that is, the optical path extends from the camera, possibly by way of a deflecting mirror, through the viewing window, through the opening in the spray shield device, and from there to the container bottom.

It is also possible, however, for the spray shield device not to have an opening but rather to have a transparent area, through which the container bottom can be observed.

In another preferred embodiment, the spray shield device has a drain opening for liquid. In this way, accumulating spray liquid can be conducted out of the spray shield device. The spray shield device is also able to reduce the contamination coming from broken containers. If, as in the state of the art, a container has broken, the glass guards underneath this container and also the adjacent guards will be contaminated. When the spray shield device is used, the adjacent viewing windows cannot become contaminated, since only a negligible percentage of the quantity of contaminating material normally present according to the state of the art will actually land on the associated viewing window. There is the option of providing a small drain opening at the base of the spray shield device specifically to handle this amount in particular.

The accuracy of the detection of the container bottoms is not significantly impaired by the slightly angled view used according to the disclosure, and the fundamental advantages of observing the complete bottom at all times are preserved. The viewing windows, as previously mentioned, are almost completely unaffected by wet containers and allow complete detection even in the case of returnable containers.

In another preferred embodiment, the viewing section is located radially inside the circular path of the container bottoms with respect to the previously mentioned projection. In this way, the overall size of the system can be kept small, especially when the observation systems are also arranged inside the circular path of the circular path of the container bottoms. In other words, the viewing sections are located inside the circular path along which the containers are guided. It is favorable that centrifugal force pushes any foreign bodies in the opposite direction, i.e., radially outward, away from the circular path. It is advantageous for a plurality of observation devices to be arranged at essentially equal distances from each other.

In another preferred embodiment, a stationary spray shield wall is provided, at least certain sections of which extend radially inside the first circular path. The corresponding section also preferably extends outside the second circular path. In particular, in the area where the bottles are transferred to the system, the spray shield wall, also called a baffle plate, can be extended to such an extent that the spray shield device continues to remain closed during the time that the bottoms are blown clean. Thus the contamination caused by the blowing-clean of the bottoms themselves, which has also been a source of contamination in the past, is avoided.

The present disclosure is also directed at a plant for inspecting containers with a system for inspecting containers of the type described above, where this plant has an acceleration carousel upstream of the system. This acceleration carousel has a plurality of holding elements, which move the containers in a predetermined manner with respect to the acceleration carousel. To stir up foreign bodies in the container, the containers are preferably rotated around their longitudinal axis, but it would also be possible to swirl them. It is especially preferred for the containers to be transferred directly from the acceleration carousel to the disclosed system.

In another preferred embodiment, the acceleration carousel has a container carrier, and this container carrier is located above the carrier plate. In other words, the plane of this container carrier is above the plane of the carrier plate.

The present disclosure can also be used to retrofit existing inspection systems. For this purpose, it is necessary only to make small changes. For example, it is possible without any significant effort to change the geometric form of the baffle plate or to position elsewhere the deflecting mirrors for the observation system. The cover area of the inspection carousel itself can also be modified relatively easily, and even the plug of the inner bottom lamp, which is used to illuminate the containers, can be easily changed.

In this way, as previously mentioned, it is possible for the machine to remain available for a longer period of time. That cleaning intervals are much farther apart, and the probability of detecting defects not actually present is significantly reduced.

The present disclosure is also aimed at a process for inspecting container bottoms in which the containers are observed by an observation device from underneath through viewing sections, where the viewing sections are arranged in viewing windows. The viewing windows themselves are mounted in a carrier plate. According to the disclosure, the containers are transported at least along certain sections of a first predetermined path a certain distance above the carrier plate, and the viewing sections are arranged with an offset to a projection of the containers in a direction perpendicular to the carrier plate.

BRIEF DESCRIPTION OF THE DRAWINGS

Additional advantages and embodiments can be derived from the attached drawings.

DETAILED DESCRIPTION

Figure 1:
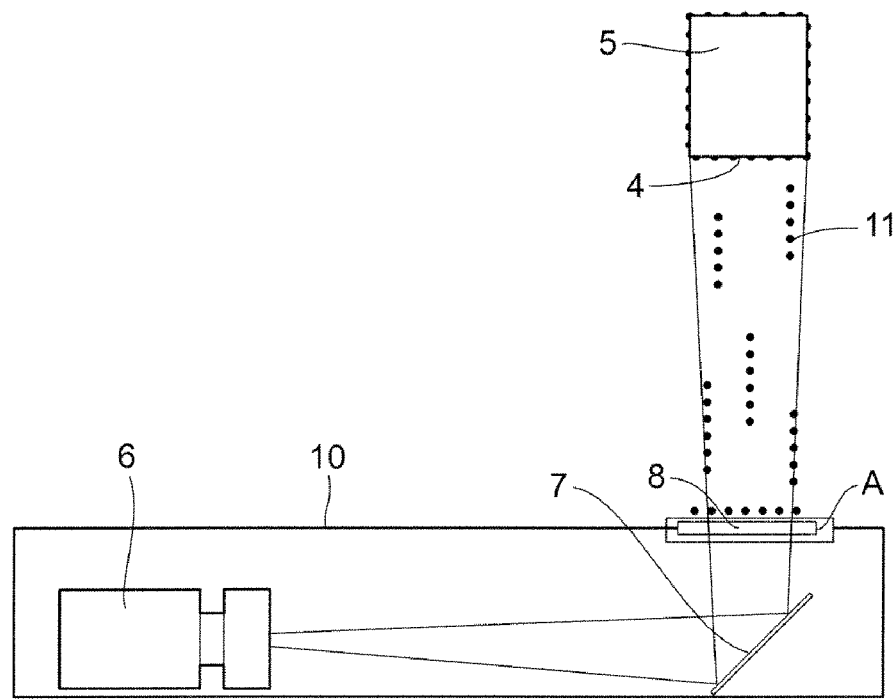
FIG. 1 shows a partial schematic diagram of an observation system according to the state of the art.

FIG. 1 shows a partial schematic diagram of a system 1 for inspecting container bottoms according to the state of the art. Reference number 5 refers to a container which has already been filled and sealed, and reference number 4 refers to the bottom of that container. This bottom 4 is observed by the inspection system. For this purpose, an observation device 6, such as a camera, is provided, which observes the container bottom 4 by way of a deflecting mirror 7. The observation proceeds through a viewing window or a glass guard 8, which is mounted in a carrier plate 10.

During operation, however, liquid 11 such as condensate falls from the container bottoms 4 and can, as indicated by reference number 11, contaminate the viewing window 8. The carrier plate 10 is part of the inspection carousel, which passes under an acceleration carousel, which transfers the containers 5. Thus it is also possible for lubricant from the drive units of the acceleration carousel to fall onto the viewing windows. More precisely, according to the state of the art, the viewing window passes directly under the drive unit of the acceleration carousel. As a result, for example, it is also possible for abraded particles in addition to liquid to land on the viewing windows. The consequence is the severe contamination of the viewing windows and thus the need to clean the viewing windows 8 at frequent intervals.

Figure 2:
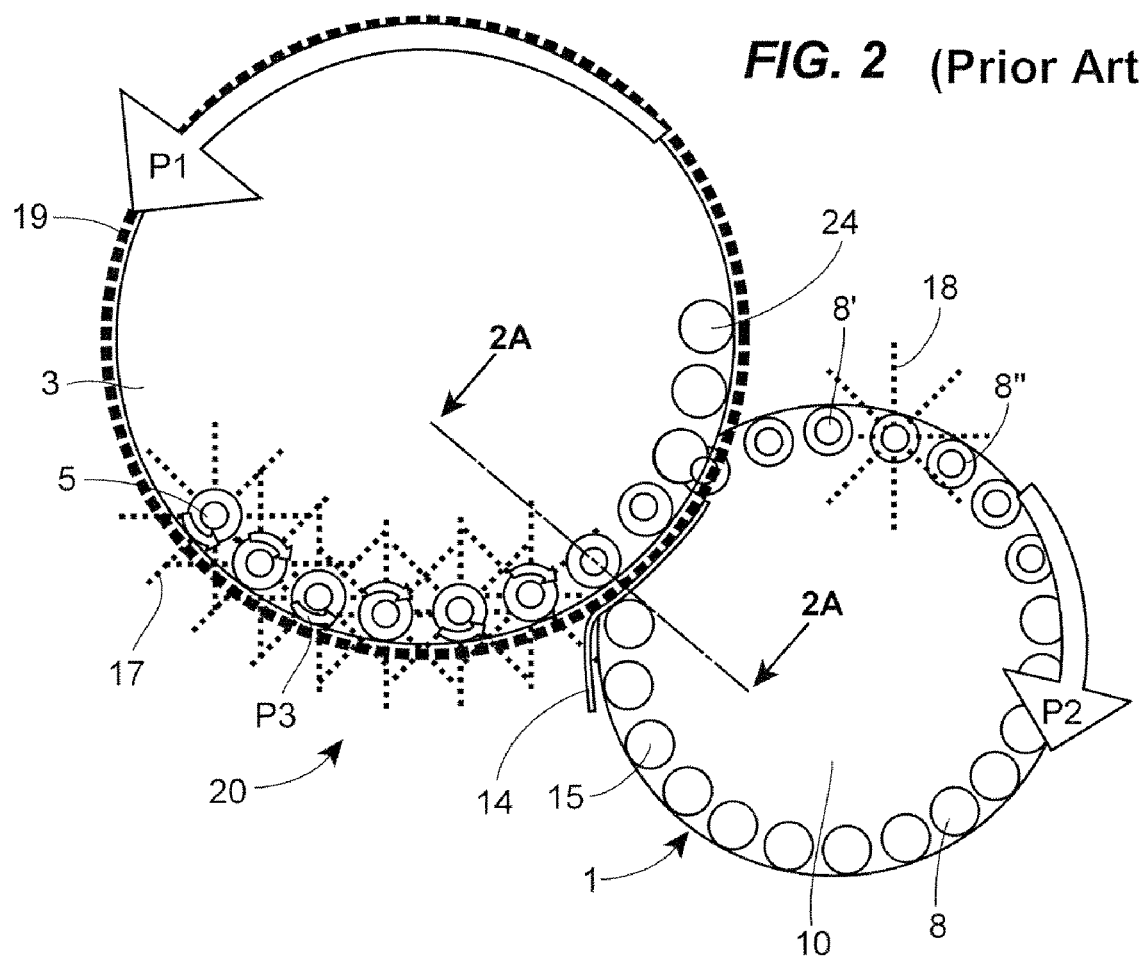
FIG. 2 shows a schematic plan diagram and FIG. 2A shows a side view of an inspection plant according to the state of the art.
Figure 2A:
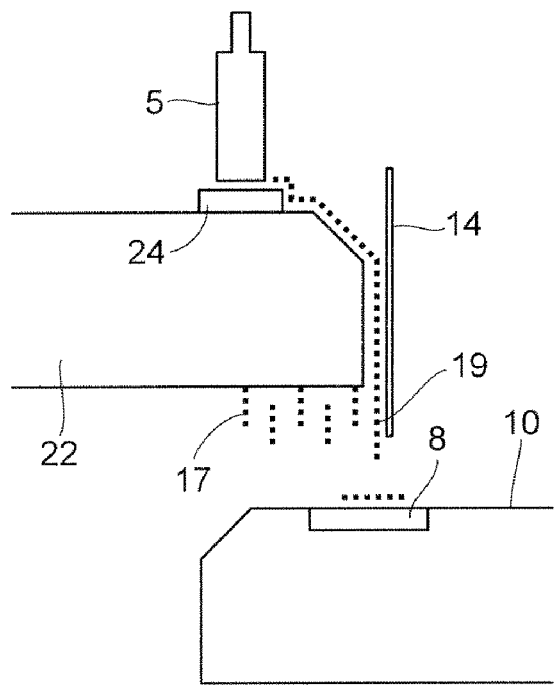

FIG. 2 shows a plan view of an inspection system according to the state of the art, while FIG. 2A shows a side view. It can be seen from FIG. 2 that certain sections of the inspection system pass below the acceleration carousel 3. In this acceleration carousel 3, the containers, as previously mentioned and as indicated by the arrows P3, are rotated around their longitudinal axis, so that the liquid in the containers is brought into motion. During this rotation, however, condensate from the containers is also spun off, which causes further contamination of the viewing windows. The acceleration carousel here rotates in the counterclockwise direction (arrow P1), and the inspection system 3 rotates in the clockwise direction (arrow P2).

Reference number 19 refers to the contamination which originates directly from the acceleration carousel 3. Reference number 24 refers to rotary tables, by means of which the containers are rotated around the longitudinal axis. This rotation can also cause contamination 17 to be spun off.

In the transfer area between the acceleration carousel 3 and the inspection system 1, the containers 4 are taken over by holding devices (not shown) and moved along the path indicated by arrow P2. According to the state of the art, the containers are held vertically above the viewing windows 8.

Although a baffle plate 14 prevents some of the contamination 17 from reaching the inspection systems 1, it does not prevent liquid dripping of the containers from landing directly on the viewing windows underneath, as indicated by reference number 15. Reference number 18 refers to the contamination which can arise as the result of the breakage of one of the containers and which can thus contaminate the adjacent viewing windows 8' and 8". FIG. 2A shows a side view of the transfer position along line A-A in FIG. 2. It can be seen that part of the acceleration carousel is located above the viewing window 8, which means that the contamination 19, 18, 17 can land on the viewing window underneath.

Figure 3:
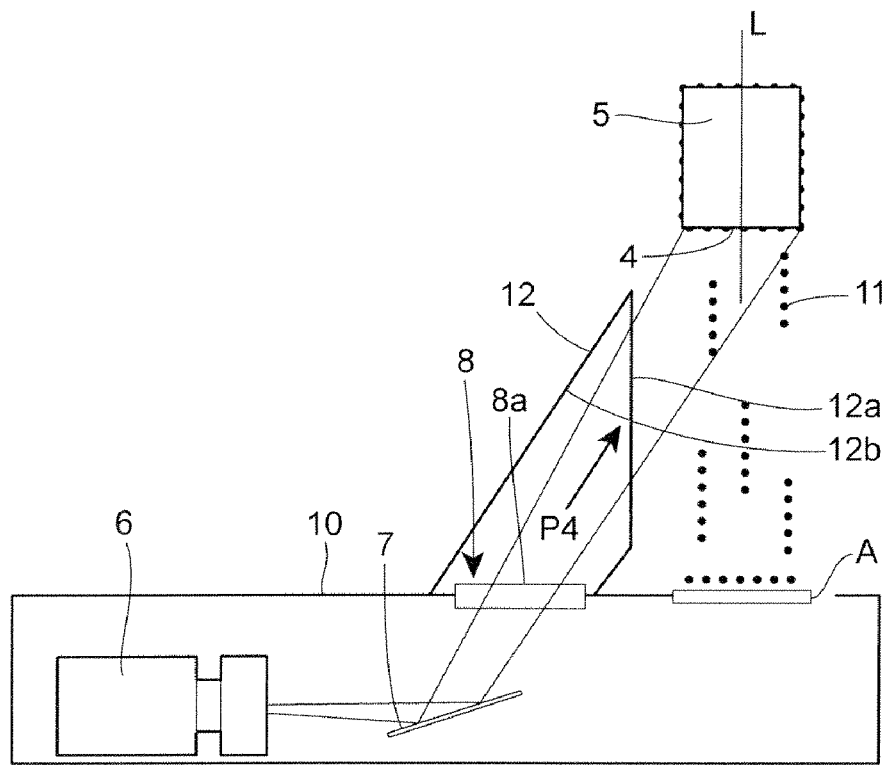
FIG. 3 shows a partial schematic diagram of an observation system according to the disclosure.
Figure 4:
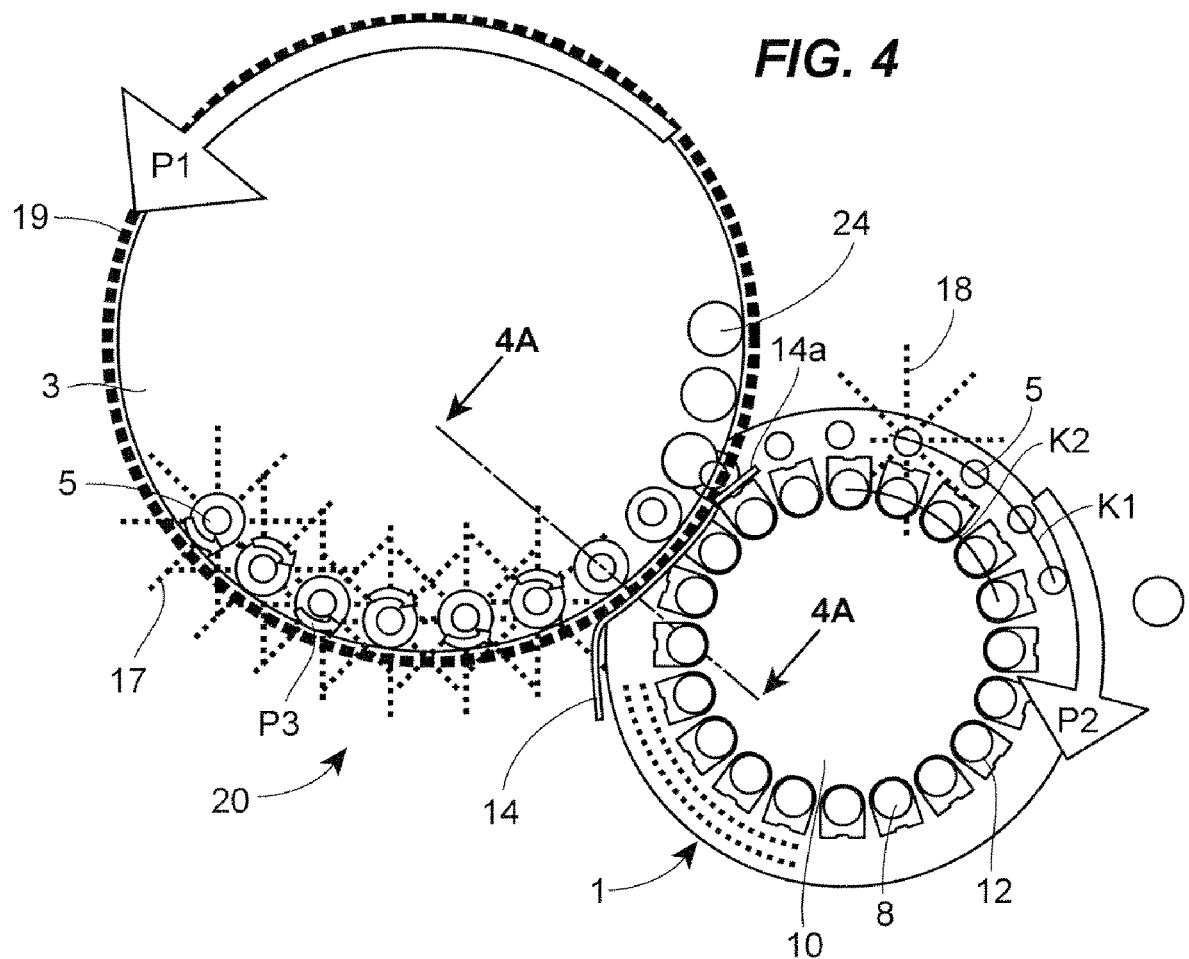
FIG. 4 shows a top view of an disclosed inspection plant.

FIG. 3 shows an disclosed inspection system or, more precisely, a plant 20 with an inspection system. It can be seen that, here, the viewing window 8, i.e., the viewing section 8a, is offset laterally from the longitudinal direction L of the containers. In other words, the container is located vertically above a section A, and this section A is laterally offset from the viewing window. This section A simultaneously represents the projection of the containers in the direction L, perpendicular to the carrier plate 10. These multiple sections A in the embodiment shown in FIG. 4 are arranged essentially in a concentric manner (along line K2) around the center point, so that, overall, when the carrier plate is viewed from above, the structure of a striped ring is created. The containers are guided by holding devices (not shown). These holders can grip different areas of the containers such as the neck area or a middle area. The containers are transported by the holders along the circular path K1 or, more precisely, the longitudinal axis of the containers are transported essentially along this circular path K1.

In this way, the goal is achieved that contamination cannot fall directly onto the viewing window 8 but rather on said area A instead. In this case as well, the observation device 6 observes the container, but here, as a result of the modified position of the deflecting mirror 7, the observation occurs not in the vertical direction but rather at an angle, as indicated by the arrow P4.

Reference number 12 refers to a spray shield device or spray water trap, which prevents the liquid which is being spun off in the radial direction from landing on the viewing window. This spray water trap has an opening 12a, through which the container bottom can be observed by the observation device 6.

More precisely, the opening or the cross section of the opening is essentially perpendicular to the carrier plate 10. The spray shield device 12 also has a slanted wall 12b, which is more-or-less parallel to the path of the beam (arrow P4).

The spray water trap 12 in particular also prevents contamination from arriving from various directions or from adjacent stations and blocks off spray water coming from the acceleration carousel 3.

FIG. 4 shows a schematic plan view of the disclosed plant. It can be seen that here the positions at which the containers 5 are guided are offset radially from the viewing windows 8. More precisely, the individual viewing windows 8 are arranged within the circular path of the containers 5 assigned to them. Reference number 12 pertains here again to the spray water trap, which prevents contamination 17, 18, 19, for example, from landing directly on the viewing windows 8.

Figure 4A:
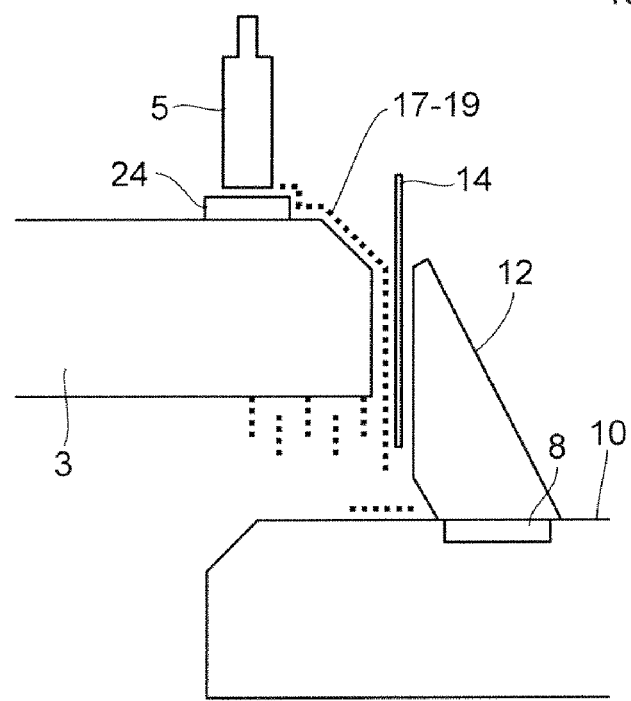

FIG. 4A again shows a side view of the disclosed inspection system. It can be seen that, in this case, too, contamination lands merely on the area or projection A and not on the viewing window 8. Here, too, the spray water trap also prevents contamination from arriving from laterally adjacent containers. As shown in FIG. 4, furthermore, the spray shield wall has been lengthened to reduce the contamination even more. In addition to the measures indicated above, it is also possible to blow off the individual viewing windows with a special air blast device to remove any still remaining residues of contamination.

Overall, as a result of the removal of the viewing window from the contamination area, contamination of the viewing window caused by the acceleration carousel 3 in particular is avoided. The spray shield wall 14 with it elongated section 14a also closes off the individual spray shield devices 12, i.e., their openings 12a, while the acceleration carousel 3 and the inspection device 1 are tangent to each other. This elongated section extends between the circular paths K1 and K2.

All of the features disclosed in the application documents are claimed as essential to the disclosure to the extent that they are novel in comparison with the state of the art, either individually or in combination.

The invention claimed is:

1. System for inspecting the bottoms of containers, comprising:
    an observation device, which observes the container bottoms, and with a plurality of viewing windows, which are arranged underneath the container bottoms and which have viewing sections, through which the observation device observes the container bottoms,
    the viewing windows being arranged in a carrier plate,
    holding devices which transport the containers a certain distance above the carrier plate,
    the viewing sections are at least partially offset from a projection of the containers in a direction perpendicular to the carrier plate, wherein the viewing sections are located completely outside the projection of the containers.

2. System according to claim 1, wherein the predetermined path is a first circular path with a predetermined radius, and in that the viewing windows are offset in a radial direction from this circular path.

3. System according to claim 1, wherein the carrier plate has a circular cross section, and the viewing windows are arranged along a second circular path which has a radius which is different from the radius of a first circular path.

4. System according to claim 1, and wherein at least one holding device is assigned to precisely one observation device and precisely one viewing section.

5. System according to claim 1, and wherein at least one spray shield device, which at least partially encloses the viewing windows, is provided above the carrier plate.

6. System according to claim 5, wherein the at least one spray shield device has a blow-off opening for liquid.

7. System according to claim 1, and wherein the viewing sections are arranged radially inside the path of the container bottoms.

8. System according to claim 1, wherein a stationary spray shield wall is provided, at least certain sections of which extend radially inside a first circular path.

9. Plant for inspecting containers with a system for inspecting container bottoms according to claim 1, and an acceleration carousel which is located upstream from the system and which has a plurality of holding elements, and which holding elements move the containers in a predetermined manner with respect to the acceleration carousel.

10. Process for inspecting the bottoms of containers, comprising:
    observing the containers through viewing sections from underneath by an observation device, and
    arranging the viewing sections in viewing windows, where the viewing windows are arranged in a carrier plate,
        transporting the container bottoms are transported along a predetermined path extending at least for a certain distance above the carrier plate and a certain distance away from this carrier plate,
    at least partially offsetting the viewing sections from a projection of the containers in a direction perpendicular to the carrier plate, wherein the viewing sections are located completely outside the projection of the containers.

11. System according to claim 1, wherein the holding devices transport the containers along a predetermined path, and the viewing windows are offset from this path.

* * * * *